[12] United States Patent
Min et al.

US010669527B2

(10) Patent No.: US 10,669,527 B2
(45) Date of Patent: Jun. 2, 2020

(54) ARTIFICIAL SKIN CULTURE CONTAINER AND METHOD FOR PRODUCING ARTIFICIAL SKIN USING SAME (71) Applicants: AMOREPACIFIC CORPORATION, Seoul (KR); SOONGSIL UNIVERSITY RESEARCH CONSORTIUM TECHNO-PARK, Seoul (KR)

(72) Inventors: Dae Jin Min, Yongin-si (KR); Sung Hoon Lee, Yongin-si (KR); Hae Kwang Lee, Yongin-si (KR); Jae Hyun Jeong, Seoul (KR); Hee Wook Ryu, Seoul (KR); Hee Jin Kim, Ansan-si (KR)

(73) Assignees: AMOREPACIFIC CORPORATION, Seoul (KR); SOONGSIL UNIVERSITY RESEARCH CONSORTIUM TECHNO-PARK, Seoul (KR)

(*) Notice: Subject to any disclaimer, the term of this patent is extended or adjusted under 35 U.S.C. 154(b) by 83 days.

(21) Appl. No.: 15/562,576

(22) PCT Filed: Mar. 22, 2016

(86) PCT No.: PCT/KR2016/002879
§ 371 (c)(1),
(2) Date: Sep. 28, 2017

(87) PCT Pub. No.: WO2016/159555
PCT Pub. Date: Oct. 6, 2016

(65) Prior Publication Data
US 2018/0087030 A1   Mar. 29, 2018

(30) Foreign Application Priority Data

Mar. 31, 2015 (KR) .................. 10-2015-0045499

(51) Int. Cl.
*C12M 1/32* (2006.01)
*C12N 5/071* (2010.01)
*C12M 3/00* (2006.01)
*A61K 35/36* (2015.01)
*A61L 27/24* (2006.01)
*A61L 27/60* (2006.01)
*C12M 3/04* (2006.01)

(52) U.S. Cl.
CPC ............ *C12N 5/0625* (2013.01); *A61K 35/36* (2013.01); *A61L 27/24* (2013.01); *A61L 27/60* (2013.01); *C12M 1/32* (2013.01); *C12M 3/00* (2013.01); *C12M 3/04* (2013.01); *C12M 21/08* (2013.01); *C12N 5/0629* (2013.01); *C12N 5/0698* (2013.01); *C12N 2533/76* (2013.01)

(58) Field of Classification Search
None
See application file for complete search history.

(56) References Cited

U.S. PATENT DOCUMENTS

| 5,906,937 A | 5/1999 | Sugiyama et al. |
| 2010/0190255 A1* | 7/2010 | Chang .................. C12N 5/0068 435/397 |

FOREIGN PATENT DOCUMENTS

| JP | H5507112 A | 10/1993 |
| JP | 06292568 A | 10/1994 |
| JP | 08243156 A | 9/1996 |
| JP | 2006115723 A | 5/2006 |
| JP | 2009524414 A | 7/2009 |
| JP | 2012080874 A | 4/2012 |
| JP | 2012235921 A | 12/2012 |
| JP | 5458259 B2 | 1/2014 |
| WO | 2007087402 A2 | 8/2007 |
| WO | 2008051228 A1 | 5/2008 |

OTHER PUBLICATIONS

Anupam Bera, et al., "Degradable/cytocompatible and pH responsive amphiphilic conetwork gels based on agarose-graft copolymers and polycaprolactone", J. Mater. Chem. B., 2015, 3, 8548-8557.
Arvind K. Singh Chandel, et al., "Effect of Polyethylene Glycol on Properties and Drug Encapsulation-Release Performance of Biodegradeable/Cytocompatible Agarose-Polyethylene Glycol-Polycaprolactone Amphiphilic Co-Network Gels", ACS Appl. Mater. Interfaces, 2016, 8, 3182-3192.
European Extended Search Report dated Nov. 6, 2018, for Application No. 16773336.9. Ganesh C. Ingavle, et al., "Using chondroitin sulfate to improve the viability and biosynthesis of chondrocytes encapsulated in interpenetrative network (IPN) hydrogels of agarose and poly(ethylene glycol) diacrylate", J. Mater Sci: Mater Med, 2012, 123, 157-170.
Hee Jin Kim, et al., "Tuning the Hydrophobicity of Agar Hydrogel with Substituent Effect", Polymer(Korea), vol. 40, No. 2, pp. 321-327 (2016).
Jinah Jang, et al., "A cell-laden nanofiber/hydrogel composite structure with tough-soft mechanical property", Applied Physics Letters, 102, 211914, 2013, 5 pp.
Arvind K. Singh Chandel, et al., "Effect of Polyethylene Glycol on Properties and Drug Encapsulation-Release Performance of Biodegradable/Cytocompatible Agarose-Polyethylene Glycol-Polycaprolactone Amphiphilic Co-Network Gels", ACS Appl. Mater. Interfaces, 2016, 8, 3182-3192.

(Continued)

*Primary Examiner* — Heidi Reese
(74) *Attorney, Agent, or Firm* — Cantor Colburn LLP (57) ABSTRACT

An artificial skin culture container according to the present invention can solve the problems of the contraction of the dermal layer of artificial skin and the detachment thereof from the culture container, which result from an interaction between collagen and fibroblasts existing in the dermal layer of artificial skin during the production of the artificial skin, by using agar and hydrophobically modifying a portion of the agar. Therefore, the use of the culture container enables to stably culture artificial skin and produce artificial skin similar to the human skin. In addition, the artificial skin culture container of the present invention comprises agar, and thus a culture solution can be supplied through a side portion as well as a lower portion of the culture container, which allows to effectively culture artificial skin.

9 Claims, 6 Drawing Sheets

(56) References Cited

OTHER PUBLICATIONS

Ganesh C. Ingavle, et al., "Using chondroitin sulfate to improve the viability and biosynthesis of chondrocytes encapsulated in interpenetrating network (IPN) hydrogels of agarose and poly(ethylene glycol) diacrylate", J Mater Sci: Mater Med., 2012, 23, 157-170.
International Search report for PCT/KR2016/002879, dated Jun. 24, 2016 (4 pages).
Junmin Zhu, et al., "Design properties of hydrogel tissue-engineering scaffolds", Expert Rev Med Devices, 2011, 8 (5):607-626.

* cited by examiner

Structure of the fibers
in the dermal layer

US 10,669,527 B2

ARTIFICIAL SKIN CULTURE CONTAINER AND METHOD FOR PRODUCING ARTIFICIAL SKIN USING SAME

TECHNICAL FIELD

The present invention relates to a culture container for culturing artificial skin and a method for producing artificial skin using the same.

BACKGROUND ART

The skin is the organ that covers the outside of the body and consists of three layers. From the outside in, they are the epidermis, the dermis and the subcutaneous layer. The epidermis is mainly composed of keratinocytes of stratified squamous epithelium. The dermis, composed of matrix proteins such as collagen fibers and elastic fibers, is located beneath the epidermis. The dermis contains blood vessels, nerves, sweat glands, etc. The subcutaneous layer is composed of adipocytes. These various cells and constituent materials interact with each other to maintain the skin shape and allow the skin to perform various functions such as thermoregulation, a barrier to external environments, etc.

Artificial skin is produced by three-dimensionally constructing a skin equivalent using skin cells and collagen, elastin, etc. which constitute the skin. It consists of living fibroblasts and keratinocytes and has similar constructional and functional properties to the real skin. Thus, it is also called a skin equivalent or a reconstructed skin. Artificial skin is a polymer complex that has similar properties to the skin mainly in elasticity, strength, and material permeability, etc. It differs from the skin in that it does not involve life phenomena as in the skin. Artificial skin is used not only for replacing (permanent engraftment type) or regenerating (temporary coating type) the skin damaged due to a burn or a wound, etc. but also in various fields such as skin physiology research, skin irritation evaluation, evaluation of effects on the skin.

However, existing artificial skins are produced by mixing collagen and dermis fibroblasts, solidifying them to obtain a dermal layer and then culturing it. During the tissue culture, collagen and fibroblast interact with each other, which inevitably leads to gradual contraction of the dermis. As a result, the dermal layer of the artificial skin is detached from the culture container during the production of the artificial skin. Furthermore, when the dermis contraction is severe, the structure of the artificial skin tissue is totally deformed and the tissue becomes physiologically abnormal, and accordingly the artificial skin has to be discarded.

CITATION LIST

Patent Literature

Japanese Patent No. 1996-243156

SUMMARY OF INVENTION

Technical Problem

In order to solve the above problems, the present invention provides a novel culture container for artificial skin, which can prevent contraction of the dermis during the production of the artificial skin. The present invention also provides artificial skin similar to the real skin in structure and function, by using the culture container.

Solution to Problem

Embodiments of the present invention provide an artificial skin culture container, which comprises agar in gel form, wherein a portion of the agar is hydrophobically modified.

Also, embodiments of the present invention provide a method for producing artificial skin in the artificial skin culture container, comprising the steps of: introducing an acellular collagen solution into the artificial skin culture container; culturing the acellular collagen solution to allow the acellular collagen solution to invade the agar of the artificial skin culture container; introducing a human dermal fibroblast solution into the artificial skin culture container and allowing the collagen solution to gel; and culturing the human dermal fibroblast solution while supplying a culture solution from outside the artificial skin culture container.

Advantageous Effects of Invention

The artificial skin culture container according to the present invention can solve the problems of the contraction of the dermal layer of artificial skin and the detachment thereof from the culture container, which result from an interaction between collagen and fibroblasts existing in the dermal layer of artificial skin during the production of the artificial skin, by agar, a portion of which is hydrophobically modified and which includes three-dimensional micropores formed therein. Therefore, the use of the culture container instead of existing cell culture containers enables to stably culture artificial skin and produce artificial skin similar to the human skin.

In addition, the artificial skin culture container of the present invention comprises agar, and thus a culture solution can be supplied through a side portion as well as a lower portion of the culture container. This enables a three-dimensional supply of a culture solution, thus allowing to effectively culture artificial skin.

DESCRIPTION OF BEST EMBODIMENTS

As used herein, the term "artificial skin" refers to a skin equivalent produced by three-dimensionally constructing a skin equivalent using skin cells and collagen, etc. which constitute the skin. It is meant to include all polymer complexes exhibiting structural and functional properties similar to the real skin.

Hereinafter, the present invention will be described in detail.

Embodiments according to the present invention provide an artificial skin culture container comprising agar in gel form, wherein a portion of the agar is hydrophobically modified.

Figure 1:
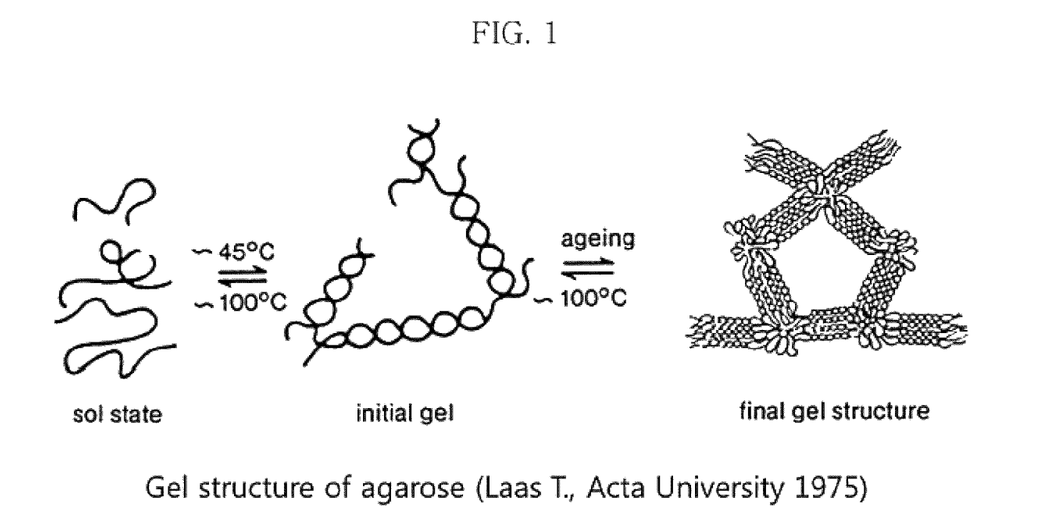
FIG. 1 is a diagram showing the gel structure of agarose.

Agar is a type of intercellular mucopolysaccharide and obtained from red algae such as gelidium. It includes sulfuric acid and is mainly composed of galactose. Agar is derived from red algae belonging to the genera *Grateloupia, Gracilaria, Hypnea* and *Gigartina* and several others, in addition to the genus *Gelidium*. Agar is mainly composed of agarose (about 70%) and agaropectin (about 30%). It is white, transparent and lustrous. It does not dissolve in cold water but does in hot water to form a sol. Specifically, when agar powders are mixed in an aqueous solution, pressurized at a constant temperature of about 100° C. to 140° C., and then cooled or aged at room temperature, they are gelled due to the physical binding of the molecules within the agar powders. This gel does not dissolve below about 85° C. It interacts with particular bacteria only and does not dissolve in salts. It is weak against acid but strong against alkali. The following Formula 1 shows the structure of agarose in agar, and FIG. 1 shows the gel structure of agarose. FIG. 1 shows the gel structure of agarose published in Laas T., Acta University 1975, which is incorporated herein by reference in its entirety.

[Formula 1]

Embodiments of the present invention may include hydrophobically-modified agar, which is obtained by substituting one or more hydrogen atoms of a portion of the agarose of the agar constituting the artificial skin culture container with a hydrophobic molecule. For example, the hydrophobic molecule may be selected from the group consisting of: one or more of $C_{12}$-$C_{18}$ alkyl, alkenyl, and acyl chains; polypropylene glycol (PPG); and polycaprolactone (PCL). However, the hydrophobic molecule is not limited thereto, as long as it can hydrophobically modify agar.

In one embodiment, when 100 agar powders before the gelation of agar is defined as one unit, and the number of the hydrophobic molecules substituted into the agar powders in one unit is defined as the degree of substitution (DS) (%), the degree of substitution of hydrophobic molecules into the agar constituting the artificial skin culture container may be 1.0% to 40%, more specifically 5.0% to 20%. If the degree of substitution of hydrophobic molecules is less than 5.0%, the hydrophobicity is low, which leads to a low binding force with collagen gel. If the degree of substitution of hydrophobic molecules is more than 20%, the affinity between the agar and collagen gel is low.

In another embodiment, the proportion of hydrophobically-modified agar may be 5.0 to 50% by weight, more specifically 5.0 to 20% by weight, based on the total weight of the agar of the artificial skin culture container. The hydrophobicity of the artificial skin culture container is determined by the weight proportion as described above. The proportion of hydrophobically-modified agar may also be adjusted depending on the desired degree of hydrophobicity, without being limited to the aforementioned weight proportion. The proportion of hydrophobically-modified agar may be selected according to the number of fibroblasts of the artificial skin to be cultured. For example, if a culture container with a high proportion of hydrophobically-modified agar is used, it is possible to produce artificial skin by culturing a large number of fibroblasts without contraction, because the container has a high binding force with collagen.

Figure 2:
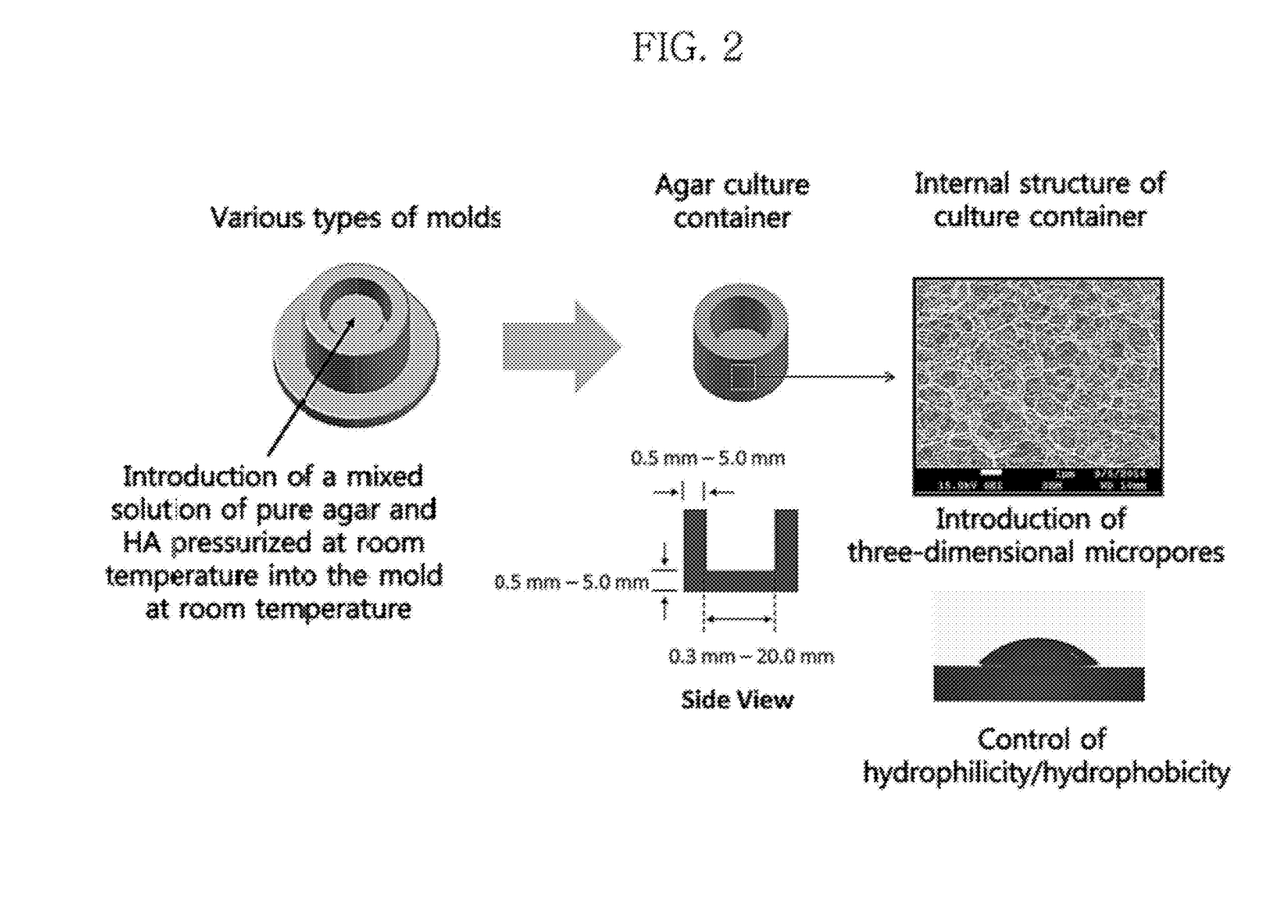
FIG. 2 shows a mimetic diagram of an artificial skin culture container and a SEM (scanning electron microscope) photograph showing the shape of three-dimensional micropores formed within the structure.

In one embodiment, for example, the thickness of the agar gel in the side portion and the lower portion of the artificial skin culture container is 0.5 to 50 mm, and the diameter of the inner bottom portion in which to culture artificial skin is 0.3 to 20.0 mm, although not limited thereto (see the culture container's mimetic diagram in FIG. 2).

According to embodiments of the present invention, the agar may comprise micropores, and the micropores may have an average diameter of 0.1 to 10 μm. The porosity of the artificial skin culture container may be 5 to 50% by volume based on the total agar volume of the artificial skin culture container. However, the porosity and the average diameter of the micropores are not limited thereto and may be adjusted according to the concentration of the agar contained in the present invention.

The micropores include those formed by hydrophobically modifying a portion of the agar, but the diameter thereof is not affected by the hydrophobicity of the agar. When artificial skin is cultured in the culture container, the collagen fibers of the artificial skin invade the culture container through the micropores, and the collagen fibers are immobilized to the culture container through three-dimensional binding with hydrophobic molecules, resulting in enhanced binding force. Thus, it is possible to prevent the problems of the contraction of the dermal layer and the detachment thereof from the culture container during culture, which result from an interaction between collagen fibers and fibroblasts existing in the dermal layer during the production of artificial skin. In addition, the use of the culture container for artificial skin production allows to freely supply a culture solution through the micropores, thus enabling to effectively culture artificial skin with normal tissues and physiological functions (see the right picture of FIG. 2). FIG. 2 shows a mimetic diagram of the artificial skin culture container according to embodiments of the present invention and a scanning electron microscope (SEM) photograph of the internal structure thereof, which includes three-dimensional micropores. The method for producing the artificial skin culture container of the present invention may employ the methods for producing an agar gel commonly used in the art, although not limited thereto.

In other embodiments, the present invention provides a method for producing artificial skin in the artificial skin culture container, comprising the steps of:

introducing an acellular collagen solution into the artificial skin culture container;

culturing the acellular collagen solution to allow the acellular collagen solution to invade the agar of the artificial skin culture container;

introducing a human dermal fibroblast solution into the artificial skin culture container and allowing the collagen solution to gel; and culturing the human dermal fibroblast solution while supplying a culture solution from outside the artificial skin culture container.

Figure 3:
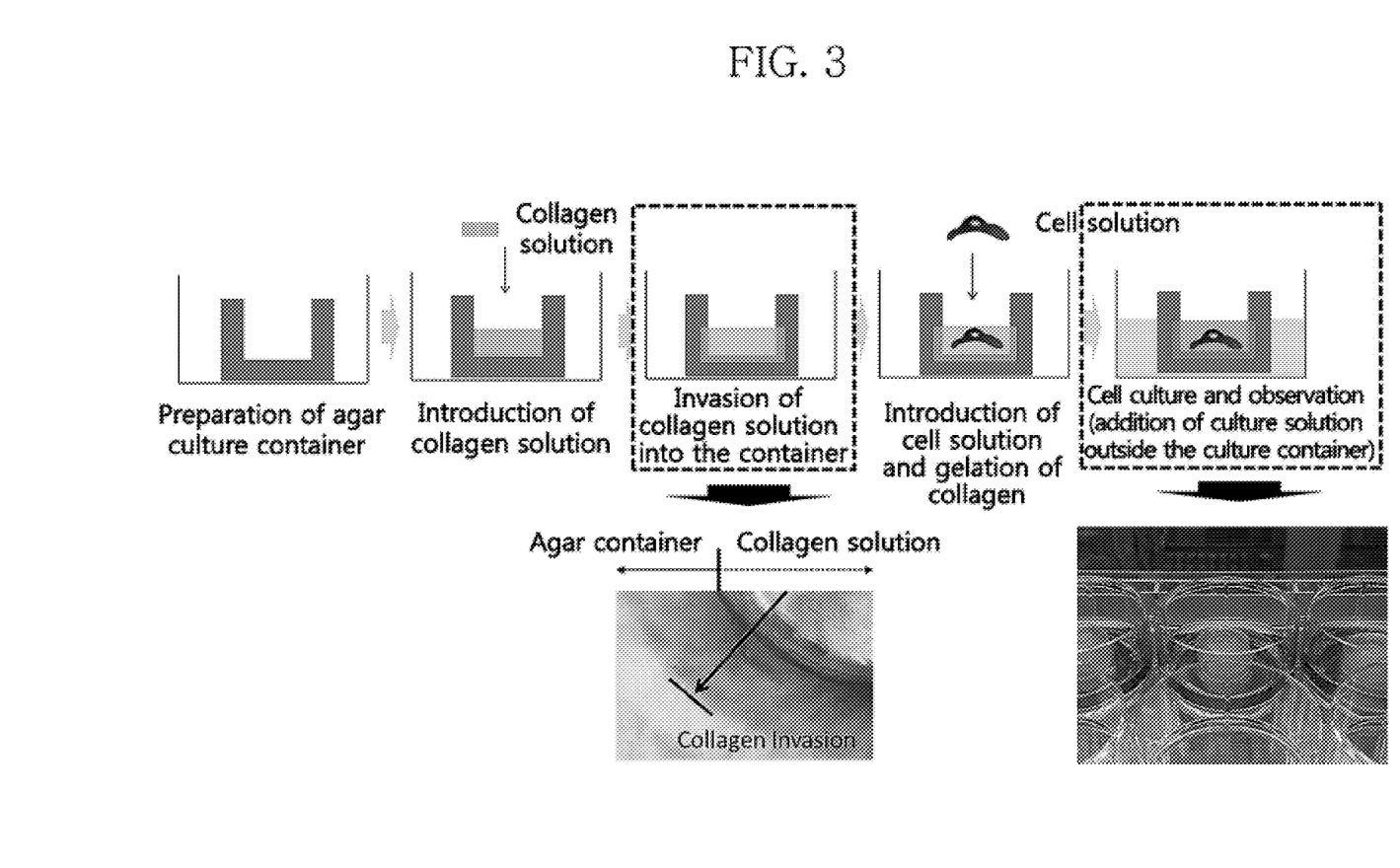
FIG. 3 is a diagram sequentially illustrating the method for producing artificial skin with the artificial skin culture container according to one embodiment of the present invention.

FIG. 3 illustrates an example of the method for producing artificial skin using the artificial skin culture container according to embodiments of the present invention. With reference to FIG. 3, the concentration of the introduced collagen is, for example, 3 mg/ml to 6 mg/ml. However, the concentration is not limited thereto and may be adjusted. In addition, the step of culturing the introduced collagen solution may comprise overnight culture at 1-10° C. or 3-5° C. In one embodiment, the step of allowing the introduced acellular collagen solution to invade the agar of the artificial skin culture container may comprise the step of allowing the collagen fibers of the collagen solution to invade the micropores in the artificial skin culture container and to be immobilized by binding to the hydrophobically-modified agar of the artificial skin culture container. The photograph below the box at the third step of FIG. 3 shows that the collagen fibers of the collagen solution invaded the container made of agar while oriented towards the container.

In addition, the step of supplying a culture solution from outside the artificial skin culture container may comprise placing the artificial skin culture container inside a chamber and supplying a culture solution into the chamber to supply the culture solution through a side portion and a lower portion of the artificial skin culture container and thereby to enable a three-dimensional supply, unlike existing containers, which allow a supply through the bottom only. It may further comprise, after the above steps, the step of culturing the artificial skin in a culture container for about 7 days. The number of fibroblasts of the cultured artificial skin may be $1.0 \times 10^3$ to $1.0 \times 10^5$ (cells/a culture insert), although not limited thereto.

Description of Embodiments

Hereinafter, the present invention will be described with reference to the following examples. The examples are for illustrative purposes only and are not intended to limit the scope of the invention. In addition, the comparative example below is only for the purpose of comparison with the examples. It is not described as prior art. It will be apparent to those skilled in the art that various modifications and variations can be made to the present invention without departing from the idea of the invention.

EXAMPLE 1

In one example of the present invention, an artificial skin culture container composed of agar gel was prepared, which comprises agar which was not hydrophobically modified (extra pure reagents, Yakuri pure chemicals Co., Ltd., Japan) and agar modified with hydrophobic octadecyl molecules (Sigma Aldrich), at a weight ratio of 10:2, wherein the total content of agar is 3% (w/v) based on the artificial skin culture container. The agar culture container had a thickness of 2 mm, an inner bottom diameter of 12 mm. The size of the micropores inside the container was about 0.5 μm.

COMPARATIVE EXAMPLE 1

In one comparative example of the present invention, an artificial skin culture container consisting of pure agar was prepared, wherein the content of agar (extra pure reagents, Yakuri pure chemicals Co., Ltd., Japan) is 3% (w/v) based on the artificial skin culture container. The agar culture container had a thickness of 2 mm, an inner bottom diameter of 12 mm. The size of the micropores inside the container was about 0.5 μm.

COMPARATIVE EXAMPLE 2

In another comparative example of the present invention, Transwell (Corning, N.Y., 14831, USA) with a diameter of 12 mm and a bottom pore size of 0.4 μm, which is a conventionally used artificial skin culture container, was prepared.

TEST EXAMPLE 1

Culture of Artificial Skin 1

Artificial skin was cultured using the artificial skin culture containers of Example 1 and Comparative Examples 1 and 2, respectively, according to the following method.

The artificial skin model produced was AmoReSkinm (AMOREPACIFIC Group, Inc.), which is a reconstructed skin composed of a dermal layer and an epidermal layer. In the artificial skin model, collagens and human dermal fibroblasts are used to form a dermal layer, onto which keratinocytes are proliferated and differentiated, thus obtaining artificial skin with similar structural/functional properties to the real skin.

First, the culture containers of Example 1 and Comparative Example 1 were dried at room temperature to lower the water content to 80% or less. 0.5 ml of a 6 mg/ml collagen solution was introduced into the dried agar culture container and cultured overnight at 4° C. After invasion of the collagen solution into the agar culture container through the culture, $1.0 \times 10^4$ human dermal fibroblasts were mixed with a collagen solution, and then 60 μl of the collagen solution (reconstitution solution, 0.22 g $NaHCO_3$, 0.477 g HEPES, 0.4 mL 1N NaOH in 10 mL $H_2O$) to gel the collagen. The artificial skin culture container was placed into a chamber. Then, while supplying a culture solution (DMEM) into the chamber to supply the culture solution three-dimensionally, culture was performed for 7 days to obtain the dermal layer of artificial skin.

In Comparative Example 2, 0.5 ml of a 6 mg/ml collagen solution was introduced, and the collagen was gelled with a collagen solution (reconstitution solution, 0.22 g $NaHCO_3$, 0.477 g HEPES, 0.4 mL 1N NaOH in 10 mL $H_2O$) mixed with $1.0 \times 10^4$ human dermal fibroblasts. Transwell was placed into a chamber, and then while supplying a culture solution (DMEM) into the chamber to supply the culture solution through the lower portion of the Transwell, culture was performed for 7 days to obtain the dermal layer of artificial skin.

$1.5 \times 10^5$ keratinocytes (human neonatal keratinocyte, HEKn, Cascade Biologics) were planted on the obtained dermal layer. Then, a keratinocyte culture medium (EpiLife, Cascade Biologics) was added inside and outside a culture insert. After overnight culture, cell adhesion was checked. Then, culture was performed for about one week while changing the medium every other day to proliferate epidermal cells. When epidermal cells proliferated sufficiently to cover the whole upper portion of the dermal layer, 1.2 mM $Ca^{2+}$ was added to the medium and the keratinocytes were allowed to differentiate for two days. All of the media were then removed and a medium was added only outside the culture insert to expose the keratinocytes to the air. While changing the medium every day, air-exposure culture was carried out for one week to form an epidermal layer and thus to obtain the final artificial skin.

Figure 4:
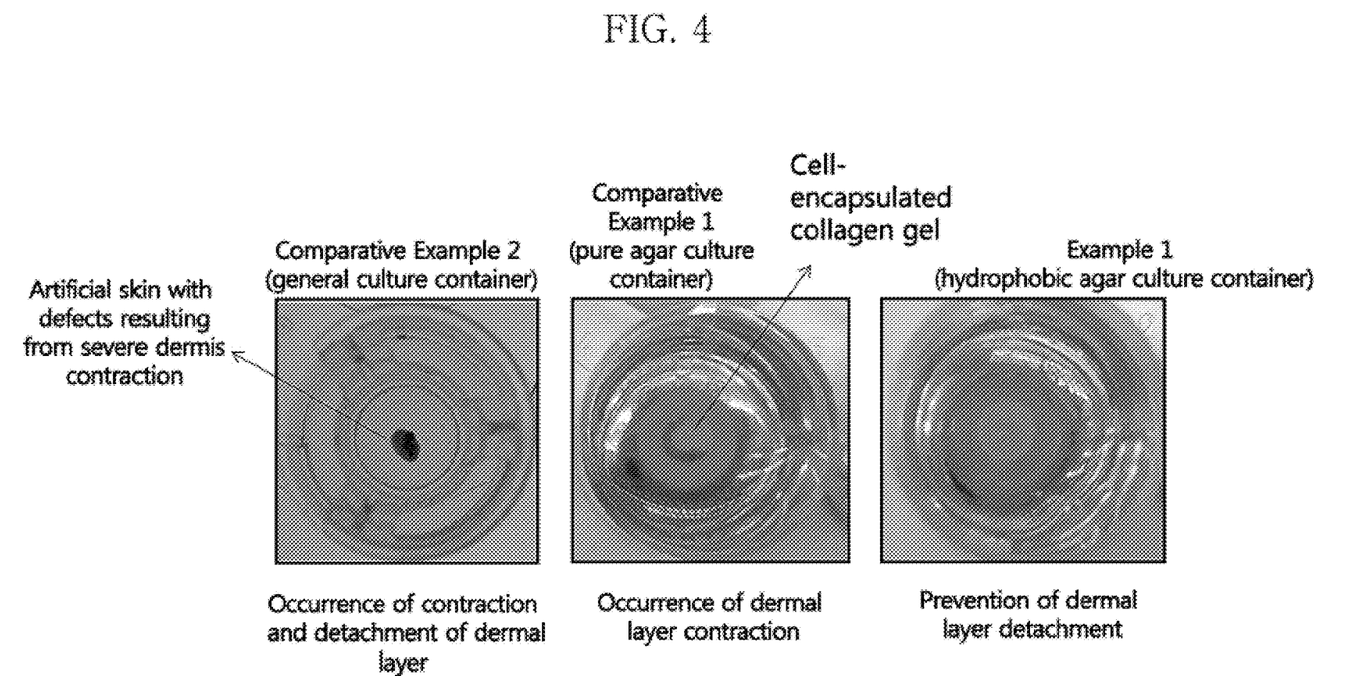
FIG. 4 shows photographs showing the artificial skin cells cultured for 7 days in a general artificial skin culture container (Comparative Example 2), a culture container made of pure agar (Comparative Example 1), or the hydrophobic agar culture container according to the present invention (Example 1).

The degree of contraction of the dermal layer was observed during the 7-day culture of the dermal layer of the artificial skin. FIG. 4 shows the photograph of the finally obtained artificial skin.

As shown in FIG. 4, in Comparative Example 2, which relates to a general artificial skin culture container, the tissue shape of the artificial skin was not maintained due to severe contraction of the dermal layer. In the culture container made of pure agar of Comparative Example 1, the artificial skin was detached from the culture container due to the interaction between collagen and fibroblasts. In contrast, the hydrophobic agar culture container of Example 1 according to the present invention prevented the contraction of the dermal layer and the detachment thereof from the culture container, due to the high binding force between the collagen fibers and the culture container.

TEST EXAMPLE 2

Culture of Artificial Skin 2

Artificial skin was cultured using the artificial skin culture containers of Example 1 and Comparative Example 1, respectively, according to the following method.

The artificial skin model produced was AmoReSkinm (AMOREPACIFIC Group, Inc.), which is a reconstructed skin composed of a dermal layer and an epidermal layer. In the artificial skin model, collagens and human dermal fibroblasts are used to form a dermal layer, onto which keratinocytes are proliferated and differentiated, thus obtaining artificial skin with similar structural/functional properties to the real skin.

First, the culture containers of Example 1 and Comparative Example 1 were dried at room temperature to lower the water content to 80% or less. 0.5 ml of a 6 mg/ml collagen solution was introduced into the dried agar culture container and cultured overnight at 4° C. After invasion of the collagen solution into the agar culture container through the culture, $1.0 \times 10^4$ human dermal fibroblasts were mixed with a collagen solution, and then 60 μl of the collagen solution (reconstitution solution, 0.22 g $NaHCO_3$, 0.477 g HEPES, 0.4 mL 1N NaOH in 10 mL $H_2O$) was added to gel the collagen. The artificial skin culture container was placed into a chamber. Then, while supplying a culture solution (DMEM) into the chamber to supply the culture solution three-dimensionally, culture was performed for 7 days to obtain the dermal layer of artificial skin.

$1.5 \times 10^5$ keratinocytes (human neonatal keratinocyte, HEKn, Cascade Biologics) were planted on the thus obtained dermal layer. Then, keratinocyte culture media (EpiLife, Cascade Biologics) were added inside and outside a culture insert. After overnight culture, cell adhesion was checked. Then, culture was performed for about one week while changing the medium every other day to proliferate epidermal cells. When epidermal cells proliferated sufficiently to cover the whole upper portion of the dermal layer, 1.2 mM $Ca^{2+}$ was added to the medium and the keratinocytes were allowed to differentiate for two days. All of the media were then removed and a medium was added only outside the culture insert to expose the keratinocytes to the air. While changing the medium every day, air-exposure culture was carried out for one week to form an epidermal layer to obtain the final artificial skin.

Figure 5:
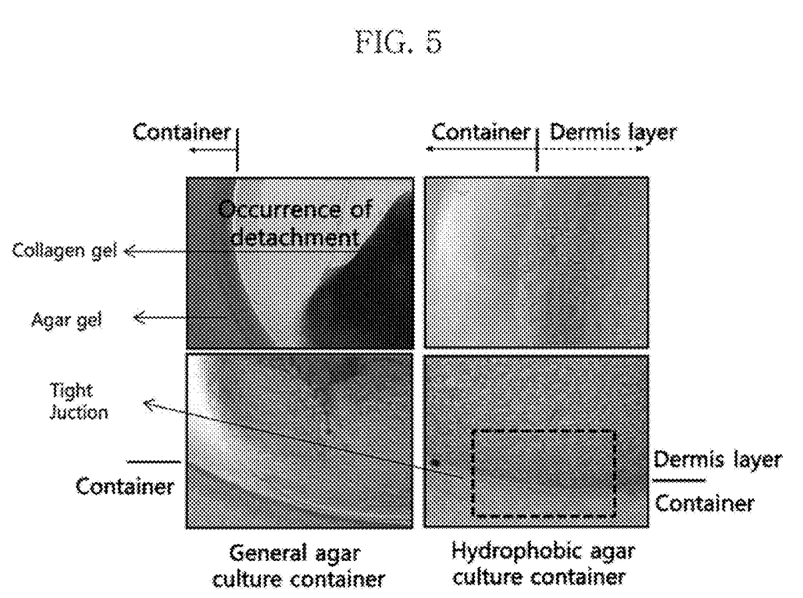
FIG. 5 shows the artificial skin cultured in a general agar culture container of Comparative Example 1, which is detached from the container (left two pictures), and the artificial skin cultured in the hydrophobically-modified agar culture container of Example 1 (right two pictures), which is tightly attached to the container without detachment.
Figure 6:
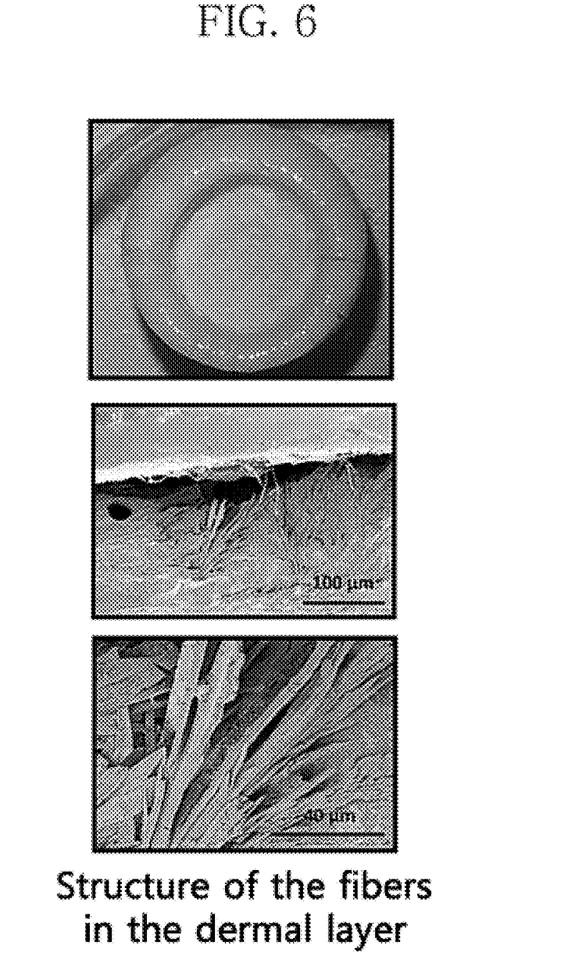
FIG. 6 is a SEM (scanning electron microscope) of the artificial skin cultured in the hydrophobically-modified agar culture container of Example 1 and then lyophilized. This shows that the collagen fibers of the dermal layer of the artificial skin are oriented towards the inside of the culture container.

FIG. 5 and FIG. 6 show the photographs of the finally obtained artificial skins, which show the detachment and attachment of the dermal layers of artificial skins to the respective agar culture containers.

The left two photographs of FIG. 5 show that the artificial skin cultured in the general agar culture container of Comparative Example 1 is detached from the container. The right two photographs of FIG. 5 show that the artificial skin cultured in the hydrophobically-modified agar container of Example 1 is tightly attached to the container without detachment. FIG. 6 shows photographs of the artificial skin cultured in the hydrophobically-modified agar culture container of Example 1, in which the collagen fibers of the dermal layer are oriented towards the inside of the culture container.

The results show that the artificial skin culture container according to the present invention can prevent the detachment of artificial skin from the container, which results from the contraction of the artificial skin during the culture thereof, thus enabling to effectively culture artificial skin, because the container is tightly attached to artificial skin during the culture of the artificial skin.

The invention claimed is:

1. An artificial skin culture container, which comprises agar in gel form, wherein a portion of the agar is hydrophobically modified,
    wherein the agar comprises agarose and agaropectin, and the portion of the agar which is hydrophobically modified is prepared by substituting one or more hydrogen atom of the agarose with a hydrophobic group or moiety, and
    wherein the hydrophobic group or moiety is selected from the group consisting of:
        one or more of $C_{12}$-$C_{18}$ alkyl, alkenyl, and acyl chains;
        polypropylene glycol (PPG); and
        polycaprolactone (PCL).

2. The artificial skin culture container according to claim 1, wherein, when 100 agar particles before the gelation of agar is defined as one unit, and the number of the hydrophobic molecules substituted into the agar particles in one unit is defined as the degree of substitution (%), the degree of substitution of hydrophobic molecules into the agar constituting the artificial skin culture container is 5.0% to 20%.

3. The artificial skin culture container according to claim 1, wherein the proportion of hydrophobically-modified agar is 5 to 50% by weight based on the total weight of the agar of the artificial skin culture container.

4. The artificial skin culture container according to claim 1, wherein the agar comprises micropores.

5. The artificial skin culture container according to claim 4, wherein the micropores have an average diameter of 0.1 to 10 μm.

6. The artificial skin culture container according to claim 4, wherein a porosity of the artificial skin culture container is 5 to 50% by volume based on the total agar volume of the artificial skin culture container.

7. A method for producing artificial skin in the artificial skin culture container according to any one of claims 1, comprising the steps of:
    introducing an acellular collagen solution into the artificial skin culture container;
    culturing the acellular collagen solution to allow the acellular collagen solution to invade the agar of the artificial skin culture container;

introducing a human dermal fibroblast solution into the artificial skin culture container and allowing the collagen solution to gel; and culturing the human dermal fibroblast solution while supplying a culture solution from outside the artificial skin culture container.

8. The method for producing artificial skin according to claim 7, wherein the step of allowing the acellular collagen solution to invade the agar of the artificial skin culture container comprises the step of allowing the collagen fibers of the collagen solution to invade the micropores in the artificial skin culture container and to be immobilized by binding to the hydrophobically-modified agar of the artificial skin culture container.

9. The method for producing artificial skin according to claim 7, wherein the step of supplying a culture solution from outside the artificial skin culture container comprises placing the artificial skin culture container into a chamber and supplying the culture solution into the chamber to supply the culture solution through a side portion and a lower portion of the artificial skin culture container.

* * * * *